United States Patent
Lutzow et al.

(10) Patent No.: US 11,484,378 B2
(45) Date of Patent: *Nov. 1, 2022

(54) HAND GRIP APPARATUS FOR RECEIVING OPERATOR INPUT IN A ROBOTIC SURGERY SYSTEM

(71) Applicant: Titan Medical Inc., Toronto (CA)

(72) Inventors: Thomas Andrew Lutzow, Providence, RI (US); Daniel P. Smith, Portsmouth, RI (US); Peter John Kenneth Cameron, Menlo Park, CA (US)

(73) Assignee: Titan Medical Inc., Toronto (CA)

( * ) Notice: Subject to any disclaimer, the term of this patent is extended or adjusted under 35 U.S.C. 154(b) by 1353 days.

This patent is subject to a terminal disclaimer.

(21) Appl. No.: 15/737,245

(22) PCT Filed: Apr. 13, 2016

(86) PCT No.: PCT/CA2016/000112
§ 371 (c)(1),
(2) Date: Dec. 15, 2017

(87) PCT Pub. No.: WO2016/201544
PCT Pub. Date: Dec. 22, 2016

(65) Prior Publication Data
US 2018/0168758 A1     Jun. 21, 2018

Related U.S. Application Data

(60) Provisional application No. 62/180,312, filed on Jun. 16, 2015.

(51) Int. Cl.
*A61B 34/00*  (2016.01)
*A61B 18/14*  (2006.01)
(Continued)

(52) U.S. Cl.
CPC .......... *A61B 34/74* (2016.02); *A61B 18/1445* (2013.01); *A61B 34/30* (2016.02);
(Continued)

(58) Field of Classification Search
CPC combination set(s) only.
See application file for complete search history.

(56) References Cited

U.S. PATENT DOCUMENTS 4,980,626 A   12/1990   Hess
5,290,386 A    3/1994   Trudeau
(Continued)

FOREIGN PATENT DOCUMENTS

| CN | 102973321 A | 3/2013 |
| CN | 103687701 A | 3/2014 |
| WO | WO 2013/018934 | 2/2013 |

OTHER PUBLICATIONS

Chinese Office Action and Search Report dated Sep. 28, 2020 in Application No. 201680041417.X.
(Continued)

*Primary Examiner* — Scott Luan
(74) *Attorney, Agent, or Firm* — Knobbe, Martens, Olson & Bear LLP

(57) ABSTRACT

A hand grip apparatus for receiving operator input includes a body having a proximal end and a distal interface end for coupling to an input apparatus. A first control lever is attached to the body and extends away from the proximal end and terminates in a finger grip for receiving one of the operator's fingers. A second control lever is attached to the body and extends away from the proximal end terminating in a thumb grip for receiving the operator's thumb. Movement of at least one of the control levers is operable to produce a first control signal representing the movement. An input control is included on the body between the grip ends
(Continued)

and has an actuator surface angled towards the finger grip end and configured to produce a second control signal in response to actuation by one of the operator's fingers.

25 Claims, 5 Drawing Sheets

(51) Int. Cl.
    *A61B 34/30*     (2016.01)
    *A61B 34/37*     (2016.01)
    *A61B 17/00*     (2006.01)
    *A61B 90/00*     (2016.01)
    *A61B 18/00*     (2006.01)

(52) U.S. Cl.
    CPC ............ *A61B 34/37* (2016.02); *A61B 90/361* (2016.02); *A61B 2017/0042* (2013.01); *A61B 2018/00595* (2013.01)

(56) References Cited

U.S. PATENT DOCUMENTS

| | | |
|---|---|---|
| 5,482,409 A | 1/1996 | Dunning |
| 5,741,113 A | 4/1998 | Bacchi |
| 6,184,868 B1 | 2/2001 | Shahoian |
| 6,231,585 B1 | 5/2001 | Takahashi |
| 6,587,750 B2 | 7/2003 | Gerbi et al. |
| 6,793,653 B2 | 9/2004 | Sanchez et al. |
| 7,074,179 B2 | 7/2006 | Wang et al. |
| 8,241,271 B2 | 8/2012 | Millman et al. |
| 8,521,331 B2 | 8/2013 | Itkowitz |
| 9,763,739 B2 | 9/2017 | Schaible et al. |
| 2003/0045900 A1 | 3/2003 | Hahnen |
| 2006/0261770 A1 | 11/2006 | Kishi et al. |
| 2008/0015631 A1 | 1/2008 | Lee |
| 2009/0058342 A1 | 3/2009 | Nihei |
| 2010/0080669 A1* | 4/2010 | Labonville ............... B25J 13/02 414/800 |
| 2013/0035697 A1 | 2/2013 | Ogawa |
| 2017/0225337 A1 | 8/2017 | Schaible et al. |

OTHER PUBLICATIONS

Liu, Feng, Ergonomics, pp. 34-38, Liaoning Art Publisher, Jul. 200.
Zhu, Xuzhang, Ergonomics, pp. 186-190, Xidian University Publisher, Jan. 2006.
International Search Report in PCT Application No. PCT/CA2016/000112 dated Jul. 21, 2016 in one page.
Written Opinion received in PCT Application No. PCT/CA2016/000112 dated Jul. 21, 2016 in four pages.
Examination Report issued in European Application No. 16810648.2 dated Apr. 7, 2020.
Extended European Search Report received in Application No. EP 16810648.2, dated Jun. 20, 2018 in 8 pages.

* cited by examiner

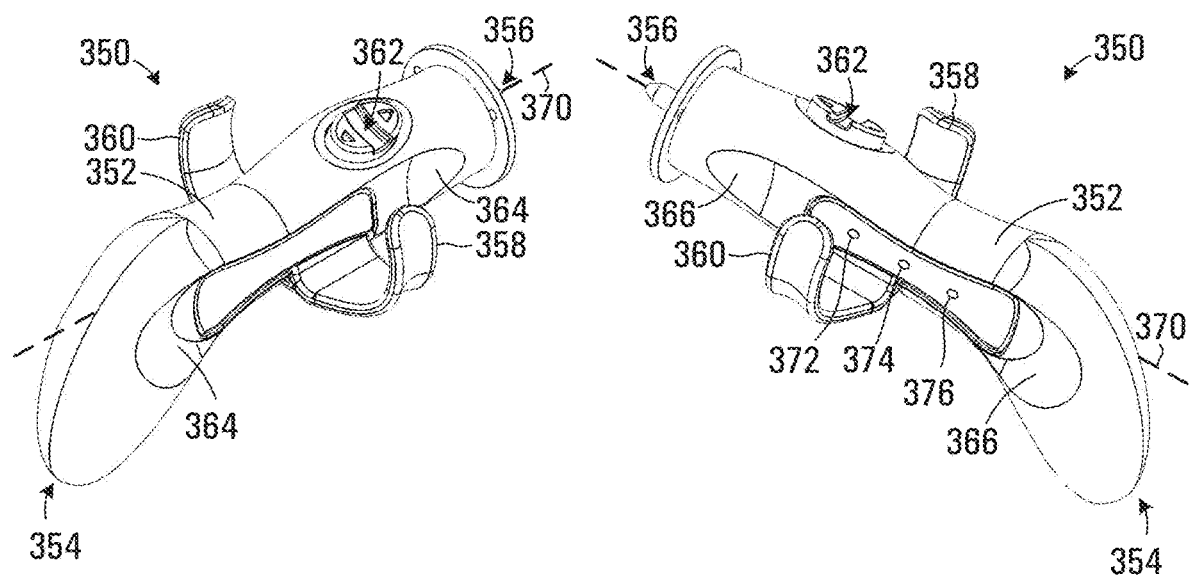
FIG. 7A  FIG. 7B
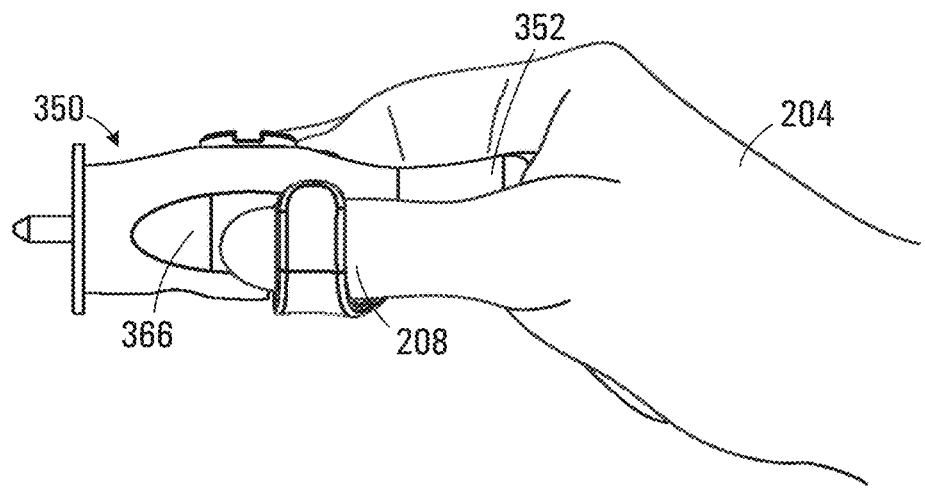
FIG. 8

HAND GRIP APPARATUS FOR RECEIVING OPERATOR INPUT IN A ROBOTIC SURGERY SYSTEM

CROSS-REFERENCE TO RELATED APPLICATION

This application is a U.S. National Phase Application under 35 U.S.C. 371 of International Application No. PCT/CA2016/000112 filed on Apr. 13, 2016 and published as WO 2016/201544 A1 on Dec. 22, 2016. This application is based on and claims the benefit of priority from U.S. Provisional Application No. 62/180,312, filed Jun. 16, 2015. The entire disclosures of all of the above applications are incorporated herein by reference.

BACKGROUND

1. Field

This disclosure relates generally to robotic surgery systems and more particularly to a hand grip apparatus for receiving operator input for controlling the robotic surgery system to perform surgical procedures.

2. Description of Related Art

Robotic surgery systems generally include an operator interface that receives operator input from a surgeon and causes corresponding movements of surgical tools within a body cavity of a patient to perform a surgical procedure. For example, the operator may grasp and move a hand grip while the operator interface senses movements of the hand grip. The operator interface and hand grip may operate to sense inputs responsive to movement of the operator's hand in several different degrees of freedom, thus providing inputs for causing the surgical tool to mimic movements of the operator's hand. Additional movements such as opening and closing of jaws of an end effector associated with the surgical tool may also be initiated in response to additional operator inputs received at the operator interface.

SUMMARY

In accordance with one disclosed aspect there is provided a hand grip apparatus for receiving operator input for controlling a surgical tool in a robotic surgery system. The apparatus includes a generally tubular body having a proximal end shaped to be grasped by a hand of the operator and a distally located interface end operably configured to be coupled to an input apparatus for controlling the surgical tool. The apparatus also includes a first control lever attached to the body at a first pivot joint and extending along the body away from the proximal end, the first control lever terminating in a finger grip end configured to receive one of the operator's fingers, the first control lever being laterally moveable away from the body about the first pivot joint. The apparatus further includes a second control lever attached to the body at a second pivot joint on a generally opposing side of the body to the first pivot joint, the second control lever extending along the body away from the proximal end and terminating in a thumb grip end configured to receive the operator's thumb, the second control lever being laterally moveable away from the body about the second pivot joint. Movement of at least one of the first and second control levers is operable to produce a first control signal representing the movement. The apparatus also includes an input control on an upper surface of the body and generally interposed between the finger and thumb grip ends, the input control having an actuator surface that is angled towards the finger grip end and being operably configured to produce a second control signal in response to actuation of the actuator surface by one of the operator's fingers.

The first control signal may include an electrical control signal and the apparatus may further include a sensor for producing the electrical control signal in response to lateral movement of at least one of the first and second control levers.

The first control signal may include a mechanical movement of a linkage coupled to at least one of the first and second control levers.

The actuator surface of the input control may be oriented such that the operator's knuckles will be generally parallel to the actuator surface when grasped by the hand of the operator in a generally neutral position.

The control button may be surrounded by a land disposed generally parallel to the actuator surface of the input control.

The first and second pivot joints may be spaced apart on the body by a distance corresponding to a distance between the metacarpophalangeal joints of the thumb and index finger of an average operator.

The first and second control levers may be sized such that when grasped by the hand of an average operator, the finger grip end and thumb grip end on the respective levers are positioned to receive distal phalanges of the operator's finger and thumb.

The finger grip may be configured to receive the operator's index finger, and the actuator surface of the input control may be angled to be actuated by the index finger moving between the finger grip and the input control.

The finger grip may be configured to receive the operator's middle finger, and the actuator surface of the input control may be angled to be actuated by the index finger.

The proximal end of the body may be configured to receive one of a plurality of different removable end caps, the removable end cap facilitating configuration of the apparatus in accordance with the operator's preference.

The proximal end of the body may have a rounded shape operable to receive and support a portion of the operator's palm when the body is grasped in the hand of the operator.

The proximal end of the body may be angled with respect to the tubular body.

The tubular body may have a neck portion interposed between the proximal end and the interface end, the neck portion having reduced cross sectional extent with respect to the proximal end.

The first and second control levers may be mechanically coupled such that movement of one of the control levers causes a corresponding opposing lateral movement of the other of the control levers.

The first and second control levers may be mounted to constrain the lateral movement of each of the levers to a range corresponding to an ergonomically comfortable lateral movement of the thumb and finger of an average operator.

At least one of the finger and thumb grip ends may include a retaining loop operably configured to retain the operator's finger or thumb for actuating the respective levers.

The retaining loop associated with the first control lever may include a loop portion and an open portion, the open portion being disposed to permit lateral movement of the operator's finger between the finger grip and the input control.

The retaining loop of the at least one of the finger and thumb grip ends may be oriented downwardly at an angle corresponding to a natural orientation of the operator's thumb or finger when the body is grasped such that the operator's palm rests on an upper surface of the body.

Each of the first and second control levers may be disposed within respective sculpted portions on generally opposing sides of the body, each extending forwardly from the proximal end toward the interface end, the respective sculpted portions being operable to receive the operator's finger and thumb when the body is grasped from behind the proximal end.

The apparatus may include at least one proximity sensor disposed to sense one of the operator's hand grasping the hand grip apparatus, and a position of the operator's hand with respect to the tubular body.

In accordance with another disclosed aspect there is provided a method for receiving operator input in a robotic surgery system. The method involves receiving a hand of the operator at a generally tubular body having a proximal end shaped for to be grasped by the operator's hand, the tubular body having a distally located interface end operably configured to be coupled to the input apparatus. The method also involves receiving one of the operator's fingers in a finger grip end of a first control lever attached to the body at a first pivot joint and extending along the body away from the proximal end, the first control lever being laterally moveable away from the body about the first pivot joint. The method further involves receiving the operator's thumb in a thumb grip end of a second control lever attached to the body at a second pivot joint on a generally opposing side of the body to the first pivot joint, the second control lever extending along the body away from the proximal end and being laterally moveable away from the body about the second pivot joint. The method also involves receiving one of the operator's fingers at an input control on an upper surface of the body and generally interposed between the finger and thumb grip ends, the input control having an actuator surface that is angled towards the finger grip end. The method further involves producing a first control signal at the interface in response to lateral opening and closing movements of the operator's finger and thumb causing corresponding lateral movement of the first and second control levers, and producing a second control signal at the interface end in response to actuation of the input control.

The method may involve receiving the first control signal at an input apparatus for controlling a surgical tool, the first control signal being operable to control opening and closing functions open of a jaw of an end effector associated with the surgical tool.

The method may involve receiving the second control signal at an input apparatus for controlling a surgical tool, the second control signal being operable to control additional functions associated with the surgical tool.

The additional functions may include one of supply of an electrical current through the jaws of the surgical tool for electro-cauterization of tissue, and functions associated with a surgical viewing system for generating views of a surgical site.

The method may involve receiving a signal from at least one proximity sensor disposed to sense one of the operator's hand grasping the hand grip apparatus and a position of the operator's hand with respect to the tubular body.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 7A is a right side perspective view of a hand grip apparatus in accordance with yet another disclosed embodiment;

FIG. 7B is a left side perspective view of a hand grip apparatus shown in FIG. 7A;

FIG. 8 is a side view of the hand grip shown in FIGS. 7A and 7B being grasped by an operator's hand.

DETAILED DESCRIPTION

Figure 1A:
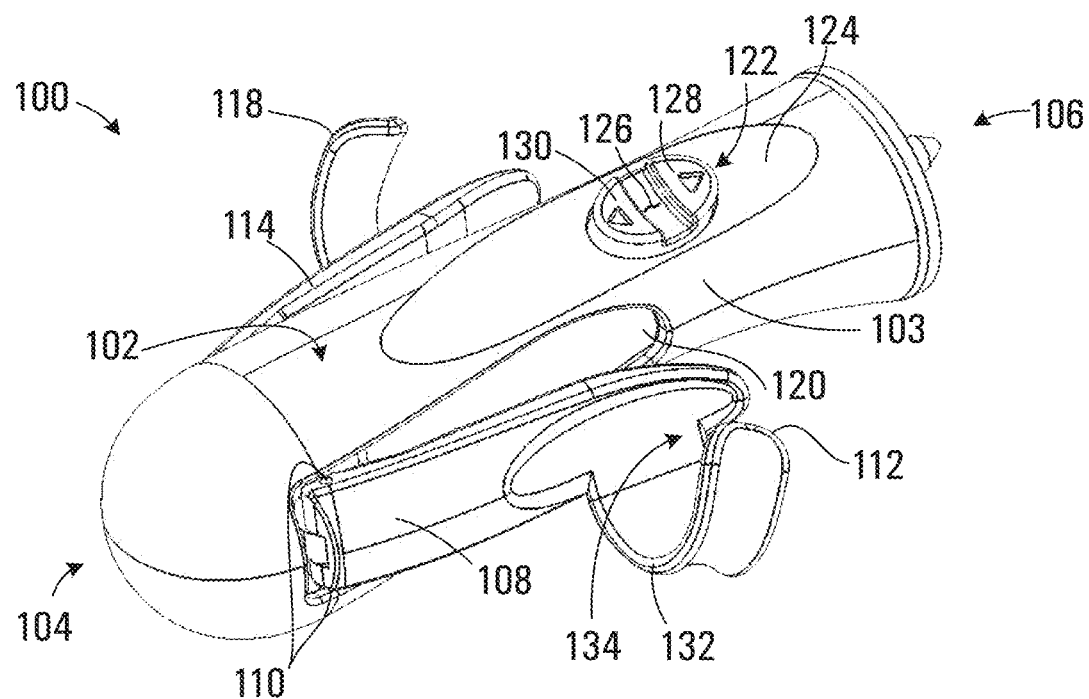
FIG. 1A is a right side perspective view of a hand grip apparatus in accordance with one disclosed embodiment.
Figure 1B:
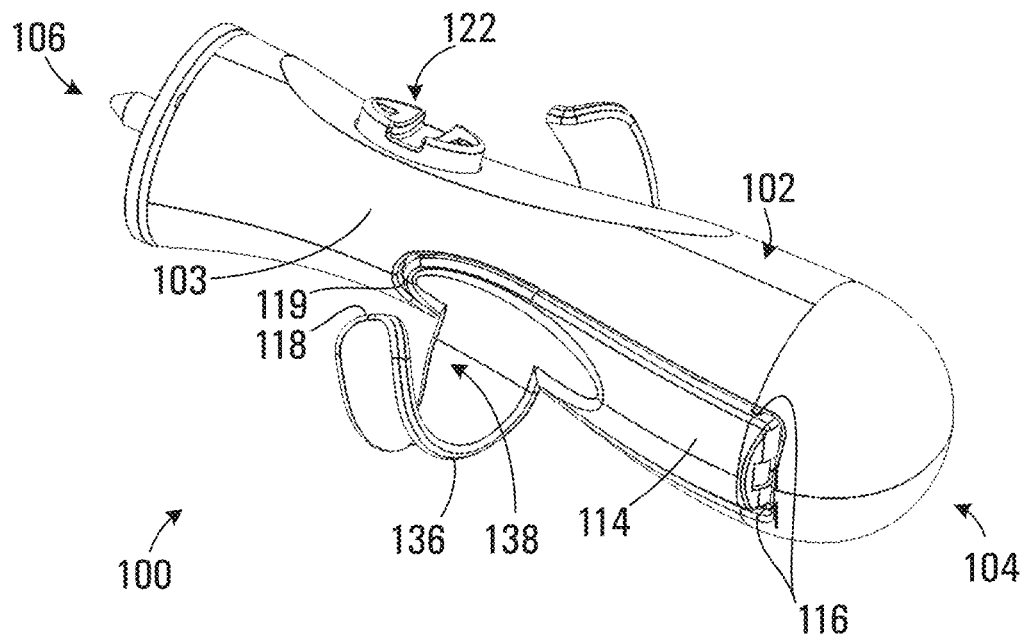
FIG. 1B is a left side perspective view of the hand grip apparatus shown in FIG. 1A.

Referring to FIGS. 1A and 1B, a hand grip apparatus according to a first embodiment of the invention is shown generally at 100. The hand grip 100 is shown in a right side perspective view in FIG. 1A and a left side perspective view in FIG. 1B. The hand grip 100 includes a generally tubular body 102 having a proximal end 104 shaped to be grasped by a hand of an operator. In the embodiment shown the proximal end 104 of the body has a rounded shape operable to receive and support a portion of the operator's palm when the body 102 is grasped in the hand of the operator.

Figure 2:
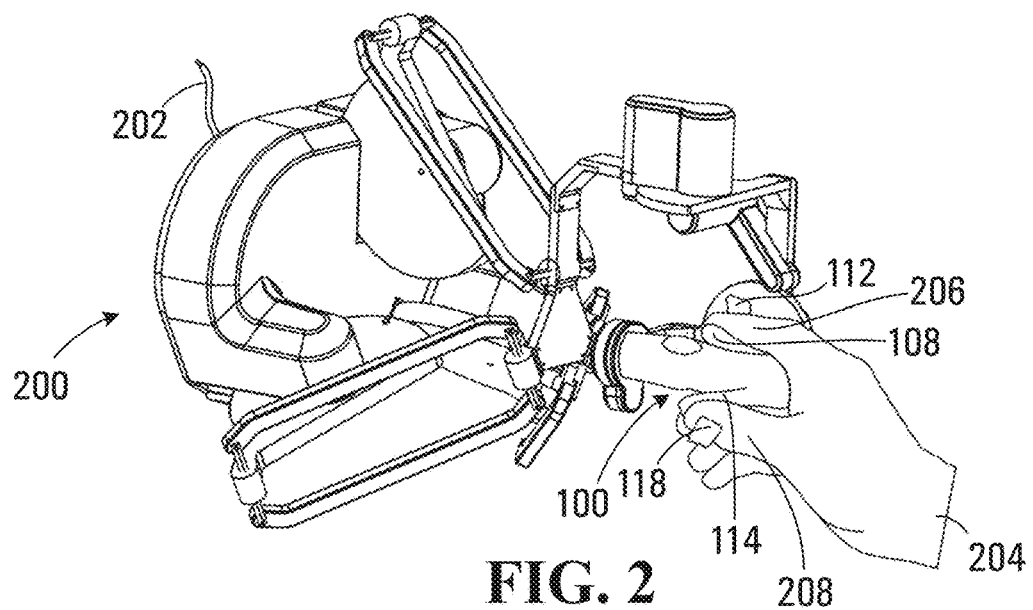
FIG. 2 is a perspective view of an input apparatus including the hand grip shown in FIG. 1.

The hand grip 100 also includes a distally located interface end 106. Referring to FIG. 2, the interface end 106 of the hand grip apparatus 100 is configured for coupling to an input apparatus 200 for controlling a surgical tool associated with a robotic surgery system (not shown). The input apparatus 200 includes an output 202 for producing signals in response to movements of the operator's hand 204. In one embodiment, the surgical tool may include an articulated tool positioner as described in detail in commonly owned patent application PCT/CA2013/001076 entitled "ARTICULATED TOOL POSITIONER AND SYSTEM EMPLOYING SAME", which is incorporated herein by reference. The input apparatus 200 may be implemented using one of the Omega series of haptic devices available from Force Dimension, of Switzerland, for example.

The input apparatus 200 and hand grip apparatus 100 are configured for operation by a right hand of the operator and in practice a left hand input apparatus and hand grip will also be provided. The left hand grip may be configured as a mirror image of the right hand grip 100 shown in FIG. 1, but may also be differently configured depending on the nature of the task the apparatus is to control.

Referring back to FIG. 1A, the hand grip 100 also includes a first control lever 108 attached to the body 102 at a first pivot joint 110. The first control lever 108 extends along the body 102 away from the proximal end 104. The first control lever 108 terminates in a finger grip end 112 configured to receive one of the operator's fingers. In the embodiment shown the finger grip end 112 is configured as a retaining loop having a loop portion 132 and an open portion 134. The loop portion 132 is configured to retain the operator's finger while the open portion 134 allows the operator's finger to be easily removed from the finger grip end 112 to permit independent lateral movement of the operator's finger. Referring to FIG. 1B, the hand grip 100 also includes a second control lever 114 attached to the body 102 at a second pivot joint 116 on a generally opposing side of the body to the first pivot joint. The second control lever 114 also extends along the body away from the proximal end 104. The second control lever 114 terminates in a thumb grip end 118 configured to receive the operator's thumb.

The first control lever 108 and the second control lever 114 are shown in an open position in FIG. 1A and in a closed position in FIG. 1B. Referring to FIG. 1A, in the embodiment shown the body 102 includes a cutout portion 120 for receiving the first control lever 108 when the first control lever is in the closed position. Referring to FIG. 1B, the body 102 also includes a cutout portion 119 and the lever 108 is received in the cutout such that a surface the lever is generally contiguous with surfaces of the body when the lever is in the closed position. The first control lever 108 is laterally moveable away from the body 102 about the first pivot joint 110 and the second control lever 114 is laterally moveable away from the body about the second pivot joint 116.

Referring to FIG. 2, the operator's index finger 206 is shown engaging the finger grip end 112 and the operator's thumb 208 is shown engaging the thumb grip end 118 of the second control lever 114. The operator is able to open and close the first and second control levers 108 and 114 by making pincer movements with the index finger and thumb respectively. The first and second control levers 108 and 114 are sized such that when grasped by the hand 204 of an average operator, the finger grip end 112 and thumb grip end 118 on the respective levers are positioned to receive distal phalanges of the operator's finger 206 and thumb 208. In this embodiment the thumb grip end 118 is also configured as a retaining loop having a loop portion 136 and an open portion 138 and the loop portion is configured to retain the operator's thumb. Alternatively, the thumb grip end 118 may be configured as a closed loop in applications where it is not necessary for the operator to frequently remove the thumb from the grip end.

The body 102 of the hand grip 100 includes a neck portion 103 portion interposed between the proximal end 104 and the interface end 106, the neck portion having a reduced cross sectional extent with respect to the proximal end 104. The neck portion 103 and the proximal end 104 together provide a bulb shaped grip, which when grasped from behind by the operator's hand is easily and comfortably retained.

Figure 3A:
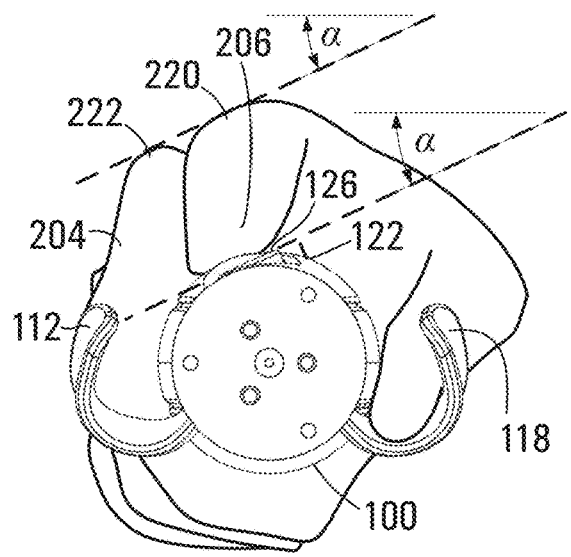
FIG. 3A is a front view of the hand grip shown in FIG. 1 being grasped by an operator's hand.

The hand grip 100 also includes an input control 122 on an upper surface of the body 102. The input control 122 is generally interposed between the finger grip end 112 and thumb grip end 118 and has an actuator surface 126 that is angled towards the finger grip end for actuation by one of the operator's fingers. The operator's hand 204 is shown grasping the hand grip 100 in FIGS. 3A and 3B. Referring to FIG. 3A, the angled actuator surface 126 of the input control 122 is comfortably located for actuation by the operator moving the index finger 206 from the finger grip end 112 to the input control 122. Alternatively, the operator may have a preference for operating the first control lever 108 using as middle finger, while the index finger 206 is held on or near the actuator surface 126 of the input control 122. In the embodiment shown the actuator surface 126 of the input control is oriented at an angle α such that the operator's knuckles 220 and 222 are generally parallel to the actuator surface 126 when the hand grip 100 is grasped by the operator's hand 204 in a generally neutral position. In one embodiment the angle α may be between about 20° and 30°. The neutral position of the hand 204 is a position in which there is a minimum of stress placed on the operator's wrist, forearm and shoulder, i.e. a comfortable position that does not induce undue fatigue.

Figure 3B:
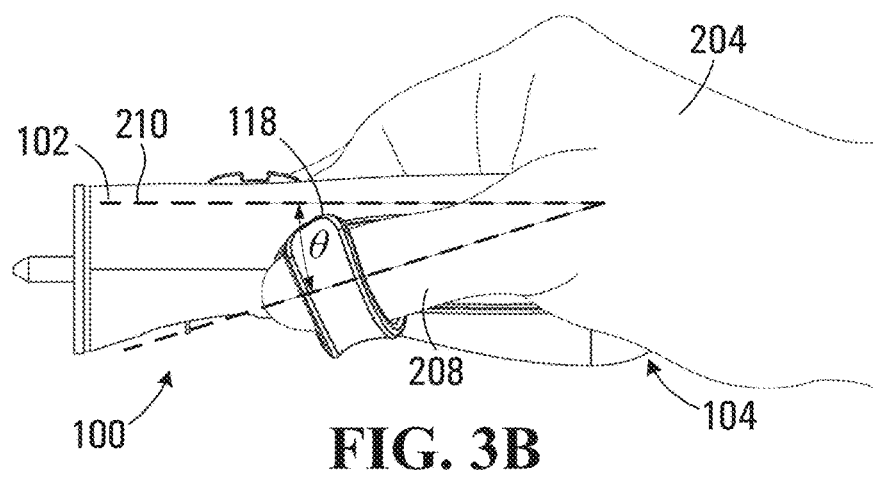
FIG. 3B is a side view of the hand grip shown in FIG. 1 being grasped by the operator's hand.

Referring to FIG. 3B, in this embodiment when the operator's hand grasps the hand grip 100 over the top of the body 102, the palm of the operator's hand 204 rests generally on an upper surface at the proximal end 104 of the body. The thumb grip end 118 is also angled downwardly at an angle θ when the body 102 is held in a horizontal orientation aligned with a horizontal axis 210. The angle θ is selected to correspond to a natural orientation of the thumb 208 when the operator's hand 204 is in a generally unstressed manner and the thumb engages the retaining loop portion of the thumb grip end 118. The finger grip end 112 may be similarly oriented at an angle corresponding to a natural orientation of the operator's finger when engaging the retaining loop portion of the finger grip 112 (not visible in FIG. 3B). In one embodiment the angle θ may be between about 10° and 25° for the operator's thumb 208 and between about 15° and 28° for the operator's index finger 206.

Referring back to FIG. 1A, in the embodiment shown the input control 122 is surrounded by a land 124, which is disposed generally parallel to the actuator surface 126 of the input control. The input control 122 may be configured to control any of a number of functions any of the surgical tool or robotic surgery system. In the embodiment shown, the input control 122 is configured as a rocker button that is operable to control a first function when a forward area 128 of the input control is pressed by the operator's finger and a second function when a rearward area 130 of the input control is pressed by the operator's finger. In other embodiments the input control 122 may be implemented using an input device or sensor configured to detect various user inputs, for example a trackpad or touchpad, track ball, joystick, optical sensor, or thermal sensor. The input control 122 is configured to produce a control signal in response to for actuation of the actuator surface by one of the operator's fingers. In one embodiment, the input control 122 may be used to control operations of an illuminator and/or camera associated with the robotic surgery system.

Figure 4A:
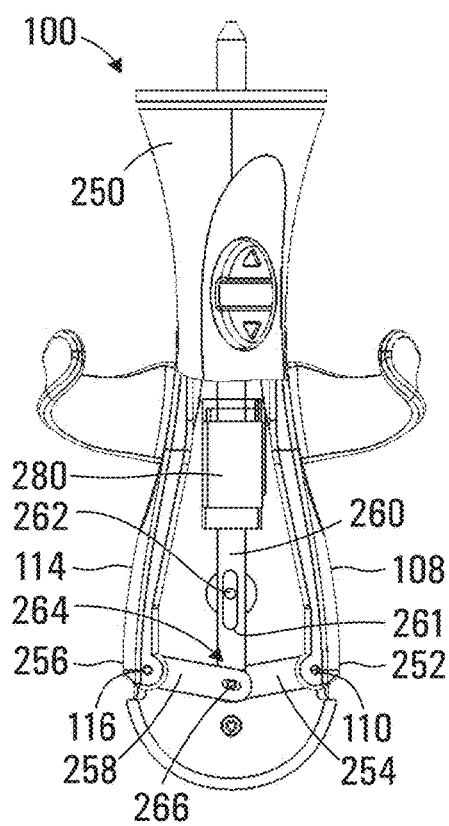
FIG. 4A is a top cutaway view of the hand grip apparatus shown in FIG. 1 with first and second levers in a closed state.
Figure 4B:
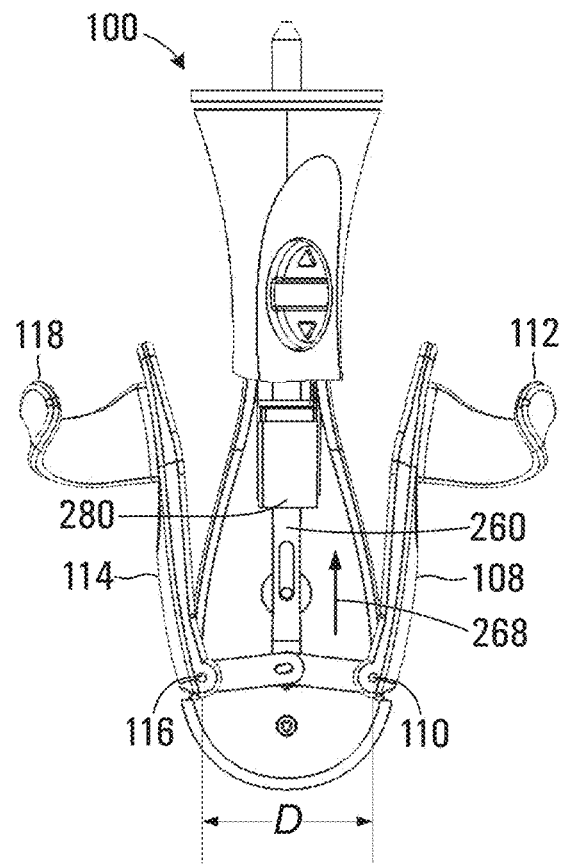
FIG. 4B is a top cutaway view of the hand grip apparatus shown in FIG. 1 with first and second levers in an open state.

The hand grip 100 is shown in cutaway view in FIGS. 4A and 4B with a portion of an upper cover 250 removed to reveal mounting details associated with the first and second control levers 108 and 114. Referring to FIG. 4A, the first control lever 108 includes a pivot end 252 mounted on the first pivot joint 110 and an actuator arm 254 extending generally laterally into the body 102 of the hand grip 100. Similarly, the second control lever 114 includes a pivot end 256 mounted on the second pivot joint 116 and an actuator arm 258 extending generally laterally into the body 102 of the hand grip 100. The hand grip 100 further includes a linkage 260 including a slot 261. The hand grip 100 also includes a guide post 262, which is received in the slot 261 and permits reciprocating movement of the linkage 260 in the direction of arrow 268. The arms 254 and 256 are each coupled to a distal end 264 of the linkage 260 at a revolute joint 266, such that movement of either of the first or second control levers 108 or 114 causes movement of the respective arm, in turn causing movement of the linkage 260. Additionally movement of either one of the arms 254 and 256 also causes a corresponding movement of the other of the arms. 12. The first and second control levers 108 and 114 are thus mechanically coupled such that movement of one of the control levers causes a corresponding opposing lateral movement of the other of the control levers. An extent of lateral movement of the first and second control levers 108 and 114 is also constrained by the length of the slot 261. In one embodiment, the slot 261 is sized to constrain movement of the levers 108 and 114 to a range corresponding to an ergonomically comfortable lateral movement of the thumb 208 and finger 206 of an average operator.

Referring to FIG. 4B, outward lateral movement of either or both of the first and second control levers 108 and 114 thus causes the linkage 260 to be advanced forwardly in the direction indicated by the arrow 268. In this embodiment, the hand grip 100 also includes a sensor 280 for producing a first control signal in response to movement of the linkage 260 caused by lateral movement of either of the first and second control levers. The sensor 280 may be implemented using a linear encoder. In other embodiments movement of the linkage 260 may be mechanically coupled through the body 102 and may mechanically interface with the input apparatus 200.

Still referring to FIG. 4B the first and second pivot joints 110 and 116 are spaced apart on the body by a distance D. In one embodiment, the spacing D between the pivot joints is selected to correspond to a distance (for an average operator) between the metacarpophalangeal joints associated with the thumb and index finger thus reducing strain on the operator's hand when operating the first and second control levers 108 and 114. When the hand grip 100 is grasped in the operator's right hand with the operator's finger 206 engaging the finger grip end 112 and the operator's thumb 208 engaging the thumb grip end 118, the metacarpophalangeal joint of the thumb is located generally above the second pivot joint 116 and the metacarpophalangeal joint (i.e. the operator's knuckle 220) of the finger is located generally above the first pivot joint 110. In a hand grip 100 configured for the operators left hand, the thumb and finger grip ends 112 and 118 would be reversed.

Figure 5:
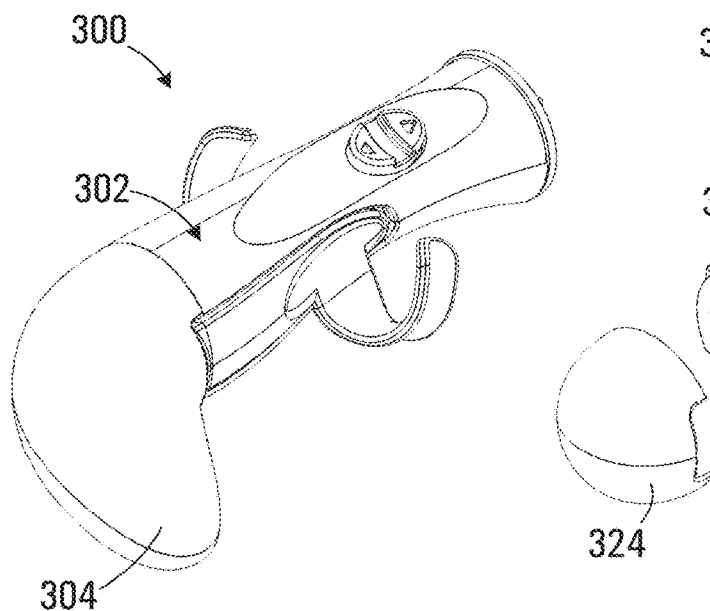
FIG. 5 is a right side perspective view of a hand grip apparatus in accordance with an alternative disclosed embodiment.
Figure 6:
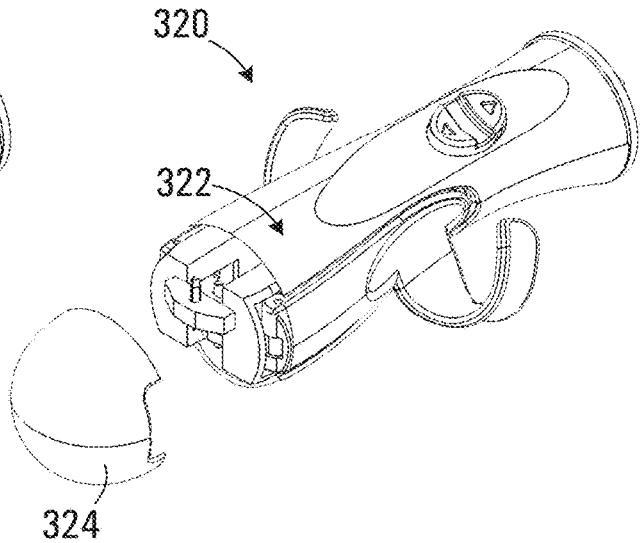
FIG. 6 is a right side perspective view of a hand grip apparatus in accordance with another disclosed embodiment.

Referring to FIG. 5, an alternative embodiment of a hand grip apparatus is shown generally at 300. The hand grip 300 has a body 302 generally configured as shown in FIG. 1 but includes a proximal end 304 of the body that is angled with respect to the tubular body. In the embodiment shown the proximal end 304 is angled in a generally lateral direction with respect to the body 302 and is configured to provide a support surface for the operator's palm when grasping the hand grip 300. Referring to FIG. 6, another embodiment of the hand grip apparatus is shown generally at 320. In this embodiment the hand grip 320 includes a removable end cap 324, which has a generally similar shape to the proximal end 104 shown in FIG. 1. The removable end cap 324 may be made easily removable by the operator to permit the operator to select an end cap in accordance with their personal preferences. The removable end cap 324 is separable from the body 322 of the hand grip 320 and may be retained on the body by a snap connection, a fastener, or other securing means. For example, a set of end caps may be provided including different lengths of the removable end cap as shown at 324 and/or different shapes of and cap, such as shape of the proximal end 304 shown in FIG. 5. The set end caps may be fabricated relatively inexpensively and permit configuration for a variety of hand sizes and operator preferences.

An alternative embodiment of a hand grip apparatus is shown generally at 350 in FIG. 7. A right hand side of the body is shown in FIG. 7A and a left hand side of the body is shown in FIG. 7B. Referring to FIG. 7A, the hand grip 350 includes a body 352 having a proximal end 354 and an interface end 356. The hand grip 350 also includes first and second control levers 358 and 360 and an input control 362 as generally described above in connection with the FIG. 1 embodiment. In this embodiment, the body 352 of the hand grip 350 includes a sculpted lateral portion 364 and the first control lever 358 is disposed on the sculpted portion. Referring to FIG. 7B, the body 352 also includes a sculpted lateral portion 366 and the second control lever 360 is disposed on the sculpted portion. The sculpted portions 364 and 366 are oriented generally parallel to a longitudinal axis 370 of the body 352. Referring to FIG. 8, the generally parallel sculpted portions 364 and 366 (only portion 366 is visible in FIG. 8) permit the operator to grasp the hand grip 350 from behind. In this embodiment, the palm of the operator's hand 204 does not rest on top of the body 352 as described in connection with the hand grip 100. Rather the palm of the operator's hand 204 is disposed behind and supported by the proximal end 354 of the hand grip 350. The proximal end 354 may be configured according to the operator's preferences as described above in connection with FIG. 5 and FIG. 6. In the embodiment shown in FIGS. 7A, 7B and 8 the hand grip 350 has a downwardly extending end cap portion while in other embodiments the hand grip may have a rounded end cap such as shown 324 in FIG. 6.

In the embodiment shown in FIG. 7B, the hand grip 350 includes a plurality of proximity sensors 372, 374, and 376 located on the second control lever 360. When the operator's hand 204 grasps the hand grip 350 the operator's thumb 208 may be positioned forwardly or rearwardly with respect to the body 352 depending on the operator's preference. The proximity sensors 372-376 generate signals for detecting the position of the operator's thumb 208, which may be used to provide an indication that the hand grip 350 is being grasped by the operator's hand 204 and also to provide information regarding the position of the operators hand on body 352 the hand grip. The proximity sensors 372, 374, and 376 may be implemented using any of a variety of proximity sensor types, for example optical and/or capacitive sensors.

Figure 9:
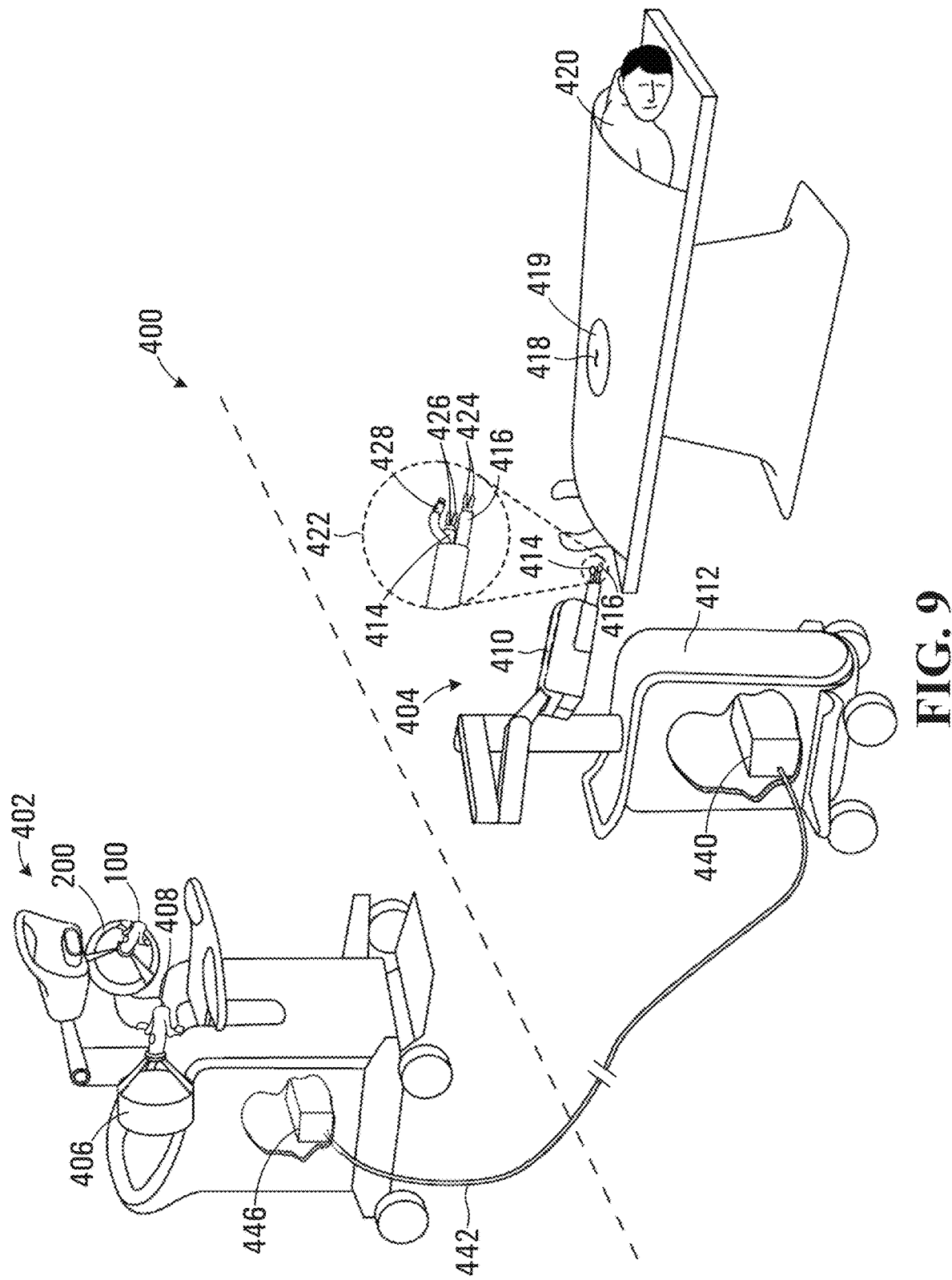
FIG. 9 is a pictorial representation of a robotic surgery system according to one disclosed embodiment.

Referring to FIG. 9, a robotic surgery system is shown generally at 400. The robotic surgery system 400 includes an input console 402 and a surgical robot 404. The input console 402 includes the input apparatus 200 and the hand grip apparatus 100 shown in FIG. 2 for operation by the operator's right hand. The input console 402 also includes an input apparatus 406 and a hand grip apparatus 408 for operation by an operator's left hand. The input console 402 also includes an interface 446 for generating control signals in response to movements and actuation of the input apparatus 200 and input apparatus 406 in response to inputs provided by the operator at the respective hand grips 100 and 408.

The surgical robot 404 includes a robotic actuator 410 carried on a surgical platform 412. The robotic actuator 410 controls surgical tools 414 and 416, which may be inserted through an incision 418 in a body wall 419 of a patient 420 to access to the surgical site (not shown) within a body cavity of the patient. The surgical tools 414 and 416 are shown in greater detail in the insert 422. In the embodiment shown the tools 414 and 416 each include a pair of opposing jaws 424 and 426. The operator, such as a surgeon for example, performs surgery on a patient 420 by manipulating the first input apparatus 200 and the second input apparatus 406 via the respective hand grips 100 and 408 on the input console 402 to control movements and operations of the surgical tools 414 and 416. The robotic actuator 410 is controlled by a processor circuit 440, which receives control signals from the input console 402 via a cable 442 or other interface. The processor circuit 440 interprets the control signals for controlling movements and operations of the viewing system 428 and the tools 414 and 416. For example, movements of the hand grips 100 and 408 are transmitted by the interface 446 to the processor circuit 440 and cause corresponding movements of the tools 414 and 416. Exemplary tool positioning devices and tools for this purpose are described in PCT/CA2013/001076, which is incorporated herein by reference. Similarly, the operator also manipulates the control levers (i.e. 108 and 114 shown in FIG. 1A) to cause the jaws 424 and 426 to open and close for performing surgical tasks such as grasping tissue, cutting, and cauterizing etc.

In embodiments that include the proximity sensors 372, 374 and 376, the proximity signals may be used to more precisely interpret the operator input based on the hand position of the operator on the hand grip 350. For example, if the user grasps the body 352 of the hand grip 350 further back, the user inputs may be scaled to amplify smaller movements by the operator's hand that are likely in this position.

In this embodiment, the surgical robot 404 also includes a viewing system 428, which may include an illuminator for illuminating the surgical site within the body cavity of the patient 420 and a camera for generating image signals. Image signals received from the viewing system are transmitted by the processor circuit 440 back to the input console 402. The input console 402 also includes a display 444 for displaying an image of the surgical site for the operator.

In one embodiment the input console 402 produces a first control signal at the interface 446 in response to lateral opening and closing movements of the operator's finger and thumb causing corresponding lateral movement of the first and second control levers. Signals representing the movements are transmitted via the cable 442 and are received and interpreted by the processor circuit 440, which produces signals for controlling the opening and closing of the respective pair of opposing jaws 424 and 426 of the tools 414 and 416. Actuation of the input control 122 similarly produces a second control signal, which is received by the processor circuit 440 and interpreted to produce signals for controlling the viewing system 428. For example, activation of the forward area 128 of the input control 122 may cause the camera to zoom in on the surgical site while actuation of the rearward area 130 may cause the camera to zoom out.

The embodiments of the hand grips 100, 300, and 350 described above provide an ergonomic interface between the operator and the input apparatus 200, 406 for receiving operator input. The respective bodies of the hand grips are shaped and configured to permit the operator to grasp the hand grips in a comfortable and strain fee manner, thus reducing operator fatigue.

While specific embodiments have been described and illustrated, such embodiments should be considered illustrative of the invention only and not as limiting the invention as construed in accordance with the accompanying claims.

What is claimed is:

1. A hand grip apparatus for receiving operator input for controlling a surgical tool in a robotic surgery system, the apparatus comprising:
   a generally tubular body having a proximal end shaped to be grasped by a hand of the operator and a distally located interface end operably configured to be coupled to an input apparatus for controlling the surgical tool;
   a first control lever attached to the body at a first pivot joint and extending along the body away from the proximal end, the first control lever terminating in a finger grip end configured to receive one of the operator's fingers, the first control lever being laterally moveable away from the body about the first pivot joint;
   a second control lever attached to the body at a second pivot joint on a generally opposing side of the body to the first pivot joint, the second control lever extending along the body away from the proximal end and terminating in a thumb grip end configured to receive the operator's thumb, the second control lever being laterally moveable away from the body about the second pivot joint, wherein movement of at least one of the first and second control levers is operable to produce a first control signal representing the movement; and
   an input control on an upper surface of the body and generally interposed between the finger and thumb grip ends, the input control having an actuator surface that is angled towards the finger grip end and being operably configured to produce a second control signal in response to actuation of the actuator surface by one of the operator's fingers, wherein the proximal end of the body is configured to receive one of a plurality of different removable end caps, the removable end cap facilitating configuration of the apparatus in accordance with the operator's preference.

2. The apparatus of claim 1 wherein the first control signal comprises an electrical control signal and further comprising a sensor for producing the electrical control signal in response to lateral movement of at least one of the first and second control levers.

3. The apparatus of claim 1 wherein movement of the at least one of the first and second control levers causes a mechanical movement of a linkage coupled to at least one of the first and second control levers, the first control signal produced in response to the movement of the linkage.

4. The apparatus of claim 1 wherein the actuator surface of the input control is oriented such that the operator's knuckles will be generally parallel to the actuator surface when grasped by the hand of the operator in a generally neutral position.

5. The apparatus of claim 1 wherein the input control is surrounded by a land disposed generally parallel to the actuator surface of the input control.

6. The apparatus of claim 1 wherein the first and second pivot joints are spaced apart on the body by a distance corresponding to a distance between the metacarpophalangeal joints of the thumb and index finger of an operator.

7. The apparatus of claim 1 wherein the first and second control levers are sized such that when grasped by the hand of an operator, the finger grip end and thumb grip end on the respective levers are positioned to receive distal phalanges of the operator's finger and thumb.

8. The apparatus of claim 1 wherein:
   the finger grip is configured to receive the operator's index finger; and the actuator surface of the input control is angled to be actuated by the index finger moving between the finger grip and the input control.

9. The apparatus of claim 1 wherein:
the finger grip is configured to receive the operator's middle finger; and
the actuator surface of the input control is angled to be actuated by the index finger.

10. The apparatus of claim 1 wherein the proximal end of the body has a rounded shape operable to receive and support a portion of the operator's palm when the body is grasped in the hand of the operator.

11. The apparatus of claim 10 wherein the proximal end of the body is angled with respect to the tubular body.

12. The apparatus of claim 10 wherein the tubular body has a neck portion interposed between the proximal end and the interface end, the neck portion having reduced cross sectional extent with respect to the proximal end.

13. The apparatus of claim 1 wherein the first and second control levers are mechanically coupled such that movement of one of the control levers causes a corresponding opposing lateral movement of the other of the control levers.

14. The apparatus of claim 1 wherein the first and second control levers are mounted to constrain the lateral movement of each of the levers to a range corresponding to an ergonomically comfortable lateral movement of the thumb and finger of an operator.

15. The apparatus of claim 1 wherein at least one of the finger and thumb grip ends comprises a retaining loop operably configured to retain the operator's finger or thumb for actuating the respective levers.

16. The apparatus of claim 15 wherein the retaining loop associated with the first control lever comprises a loop portion and an open portion, the open portion being disposed to permit lateral movement of the operator's finger between the finger grip and the input control.

17. The apparatus of claim 15 wherein the retaining loop of the at least one of the finger and thumb grip ends is oriented downwardly at an angle corresponding to a natural orientation of the operator's thumb or finger when the body is grasped such that the operator's palm rests on an upper surface of the body.

18. The apparatus of claim 1 wherein each of the first and second control levers are disposed within respective sculpted portions on generally opposing sides of the body, each extending forwardly from the proximal end toward the interface end, the respective sculpted portions being operable to receive the operator's finger and thumb when the body is grasped from behind the proximal end.

19. The apparatus of claim 1 further comprising at least one proximity sensor disposed to sense one of:
the operator's hand grasping the hand grip apparatus; and
a position of the operator's hand with respect to the tubular body.

20. A method for receiving operator input in a robotic surgery system, the method comprising:
receiving a hand of the operator at a generally tubular body having a proximal end shaped for to be grasped by the operator's hand, the tubular body having a distally located interface end operably configured to be coupled to the input apparatus;
receiving one of the operator's fingers in a finger grip end of a first control lever attached to the body at a first pivot joint and extending along the body away from the proximal end, the first control lever being laterally moveable away from the body about the first pivot joint;
receiving the operator's thumb in a thumb grip end of a second control lever attached to the body at a second pivot joint on a generally opposing side of the body to the first pivot joint, the second control lever extending along the body away from the proximal end and being laterally moveable away from the body about the second pivot joint;
receiving one of the operator's fingers at a input control on an upper surface of the body and generally interposed between the finger and thumb grip ends, the input control having an actuator surface that is angled towards the finger grip end;
producing a first control signal at the interface in response to lateral opening and closing movements of the operator's finger and thumb causing corresponding lateral movement of the first and second control levers;
producing a second control signal at the interface end in response to actuation of the input control; and
receiving a signal from at least one proximity sensor disposed to sense one of the operator's hand grasping the hand grip apparatus and a position of the operator's hand with respect to the tubular body.

21. The method of claim 20 further comprising receiving the first control signal at an input apparatus for controlling a surgical tool, the first control signal being operable to control opening and closing functions open of a jaw of an end effector associated with the surgical tool.

22. The method of claim 21 further comprising receiving the second control signal at an input apparatus for controlling a surgical tool, the second control signal being operable to control additional functions associated with the surgical tool.

23. The method of claim 22 wherein the additional functions comprise one of:
supply of an electrical current through the jaws of the surgical tool for electro-cauterization of tissue; and
functions associated with a surgical viewing system for generating views of a surgical site.

24. A hand grip apparatus for receiving operator input for controlling a surgical tool in a robotic surgery system, the apparatus comprising:
a generally tubular body having a proximal end shaped to be grasped by a hand of the operator and a distally located interface end operably configured to be coupled to an input apparatus for controlling the surgical tool;
a first control lever attached to the body at a first pivot joint and extending along the body away from the proximal end, the first control lever terminating in a finger grip end configured to receive one of the operator's fingers, the first control lever being laterally moveable away from the body about the first pivot joint;
a second control lever attached to the body at a second pivot joint on a generally opposing side of the body to the first pivot joint, the second control lever extending along the body away from the proximal end and terminating in a thumb grip end configured to receive the operator's thumb, the second control lever being laterally moveable away from the body about the second pivot joint, wherein movement of at least one of the first and second control levers is operable to produce a first control signal representing the movement; and
an input control on an upper surface of the body and generally interposed between the finger and thumb grip ends, the input control having an actuator surface that is angled towards the finger grip end and angled away from the thumb grip end so that the input control is closer to the finger grip end than the thumb grip end, the input control being operably configured to produce a second control signal in response to actuation of the actuator surface by one of the operator's fingers.

25. The apparatus of claim 24 wherein movement of the at least one of the first and second control levers causes a mechanical movement of a linkage coupled to at least one of the first and second control levers, the first control signal produced in response to the movement of the linkage.

\* \* \* \* \*